United States Patent
Gerlich et al.

(12) 
(10) Patent No.: US 6,303,825 B1
(45) Date of Patent: Oct. 16, 2001

(54) METHOD OF STARTING UP LOOP REACTOR SYSTEMS IN WHICH AT LEAST ONE EXOTHERMIC REACTION IS TO BE CARRIED OUT

(75) Inventors: Otto Gerlich, Gladbeck; Michael Kleine-Boymann, Bottrop; Hermann Schmidt; Juergen Volke, both of Gladbeck, all of (DE)

(73) Assignee: Phenolchemie GmbH & Co. KG, Gladbeck (DE)

( * ) Notice: Subject to any disclaimer, the term of this patent is extended or adjusted under 35 U.S.C. 154(b) by 0 days.

(21) Appl. No.: 09/524,741

(22) Filed: Mar. 13, 2000

(30) Foreign Application Priority Data

Mar. 12, 1999 (DE) ............................................... 199 11 024

(51) Int. Cl.[7] ........................... C07C 45/00; B32B 27/04; B01J 8/18; B01F 23/90; B01F 5/06
(52) U.S. Cl. .......................... 568/385; 422/132; 422/139; 422/140; 422/231; 366/336
(58) Field of Search ..................................... 422/132, 231, 422/139, 140; 366/336; 568/385

(56) References Cited

FOREIGN PATENT DOCUMENTS 0 589 588 A1     3/1994   (EP) .

Primary Examiner—Samuel Barts
Assistant Examiner—Elvis O. Price
(74) Attorney, Agent, or Firm—Oblon, Spivak, McClelland, Maier & Neustadt, P.C.

(57) ABSTRACT

The present invention provides a method of starting up a loop reactor system, which method includes heating a reaction mixture present in the loop reactor system with the heat of reaction of at least one exothermic reaction occurring in the loop reactor system. The method of the invention makes possible an inexpensive, reliable and simple start-up of loop reactor systems, since the heat liberated when carrying out an exothermic reaction is utilized for heating the reaction mixture present in the loop reactor. Use of the method of the invention makes it unnecessary to switch heat exchangers over from coolant to heat transfer media such as steam. Since the method of the invention is able to heat up the reaction mixture in the loop reactor system more rapidly than in conventional methods, the number and the amount of by-products formed by secondary reactions during the start-up phase is reduced. In addition, the method of the invention reduces the corrosive stress on the heat exchangers since none of the heat exchangers need be at a temperature significantly higher than the temperature of the reaction mixture in the loop reactor system.

27 Claims, No Drawings

METHOD OF STARTING UP LOOP REACTOR SYSTEMS IN WHICH AT LEAST ONE EXOTHERMIC REACTION IS TO BE CARRIED OUT

BACKGROUND OF THE INVENTION

1. Field of the Invention

The invention relates to a new method of starting up loop reactor systems in which at least one exothermic reaction is to be carried out.

2. Discussion of the Background

Loop reactor systems are frequently used for carrying out exothermic reactions since the reaction can be controlled in a simple manner via the amount of product which is circulated.

A typical reaction that can be carried out in a loop reactor is the acid catalyzed cleavage of cumene hydroperoxide (CHP) into phenol and acetone. Phenol is a valuable basic organic chemical. It is used, for example, for the production of bisphenol A, ε-caprolactam, adipic acid, alkylphenols, chlorophenols, antioxidants, plasticizers and phenolic resins. The annual worldwide capacity for the production of phenol is about 6 million metric tons (Weissermehl, Arpe, Industrial Organic Chemistry, Third Edition, 1997, VCH Weinheim).

The most important method of preparing phenol is the oxidation of cumene wherein cumene hydroperoxide is first formed and then cleaved in the presence of an acid catalyst to form phenol and acetone. This cleavage is preferably carried out in a loop reactor system, with the loop reactors being run at an optimum operating temperature of 50 to 90° C.

EP 0 589 588 discloses a process for preparing phenol, acetone and a methylstyrene that uses a loop reactor system having three loop reactors for the cleavage of CHP. The operating temperatures of the loop reactors reported for this process are 50 to 62° C. for the first loop reactor, 62 to 57° C. for the second loop reactor and 57 to 50° C. for the third loop reactor.

The procedure that is typically used for starting up such loop reactor systems is, e.g., in the cleavage of CHP, to circulate a reaction mixture that predominantly includes the products and the catalyst through the loop reactor system and then heat the system to the reaction temperature. This is usually done by switching over one of the heat exchangers in the loop reactor system from a coolant to a heat transfer medium such as steam while interrupting the coolant flow through any other heat exchangers present in the system. The steam, which transfers its heat to the circulating reaction mixture in the heat exchanger, allows the reaction mixture to be heated to the start up temperature. This is supposed to ensure that the exothermic reaction does not continue in the downstream systems without sufficient cooling.

The above method of starting up loop reactor systems in which an exothermic reaction is to proceed is relatively complicated since at least one heat exchanger must be switched over from coolant to steam, and the coolant must first be removed from the heat exchanger before the steam can be passed into the heat exchanger. If there are any leaks in the shut-off valves for the coolant in the heat exchangers, which have only been turned off and from which the coolant has not been removed, the heating-up process may take a relatively long time. For this reason, comprehensive additional technical facilities become necessary.

In the above-noted method for heating up the reaction mixture in a loop reactor system, it is also possible for the products present in the reaction mixture, e.g. phenol and acetone, to react with the catalyst present in the reaction mixture to form undesired by-products during the long heating-up time, which undesirably results in the loss of product.

In addition, when steam is supplied to the heat exchanger, the temperature at the heat exchanger can rise above the temperature that normally prevails during the reaction so that when sulfuric acid is used as catalyst, e.g. in the cleavage of CHP, the heat exchanger is exposed to an increased corrosive stress owing to the high temperature.

SUMMARY OF THE INVENTION

It is therefore an object of the invention to provide a method of starting up loop reactors in which an exothermic reaction is to occur.

Another object of the invention is to provide an inexpensive, reliable and simple method of starting up a loop reactor system.

Another object of the invention is to provide a method that eliminates the need to switch heat exchangers over from coolant to heat transfer media.

Another object of the invention is to provide a method for heating up a reaction mixture in a loop reactor system more rapidly than in conventional methods.

Another object of the invention is to reduce the number and the amount of by-products formed by secondary reactions during the start-up phase of a loop reactor system.

Another object of the invention is to reduce the corrosive stress on heat exchangers in a loop reactor system.

Another object of the invention is to provide a method of starting up a loop reactor system in which, ideally, none of the heat exchangers are at a temperature significantly higher than the temperature of the reaction mixture in the loop reactor system.

These and other objects of the invention are surprisingly achieved by a method of starting up a loop reactor system, which method includes:

heating a reaction mixture present in the loop reactor system with the heat of reaction of at least one exothermic reaction occurring in the loop reactor system.

The method of the invention makes possible an inexpensive, reliable and simple start-up of loop reactor systems, since the heat liberated when carrying out an exothermic reaction is utilized for heating the reaction mixture present in the loop reactor. Use of the method of the invention makes it unnecessary to switch heat exchangers over from coolant to heat transfer media such as steam. Since the method of the invention is able to heat up the reaction mixture in the loop reactor system more rapidly than in conventional methods, the number and the amount of by-products formed by secondary reactions during the start-up phase is reduced. In addition, the method of the invention reduces the corrosive stress on the heat exchangers since none of the heat exchangers need be at a temperature significantly higher than the temperature of the reaction mixture in the loop reactor system.

DETAILED DESCRIPTION OF THE INVENTION

Various other objects, features and attendant advantages of the present invention will be more fully appreciated as the same becomes better understood from the following detailed description of the preferred embodiments of the invention.

Loop reactors are frequently utilized for carrying out exothermic reactions. At the beginning of these reactions, it is often necessary to bring the reaction mixture circulated through the reactor to a particular temperature dependent on the type of reaction. Hitherto, heat exchangers which are to remove excess heat from the reaction mixture after commencement of the reaction have for this purpose customarily been supplied with a heat transfer medium such as steam instead of a coolant during start-up in order to heat the circulating reaction mixture to the reaction temperature. This procedure is relatively cumbersome and time-consuming. The method of the invention allows the initial temperatures of exothermic reactions of the circulating reaction mixture to be set simply and quickly. The method preferably makes use of the heat liberated in the exothermic reaction by adding, restricted in terms of time and amount, starting material mixture to the circulating reaction mixture in such an amount that the starting materials can no longer be detected in the part of the circulating reaction mixture taken off downstream of the reactor. The addition of starting material mixture is preferably repeated until all the reaction mixture being circulated has reached the reaction temperature. The method of the invention can be used, for example, for the start-up of the cleavage reaction in the cleavage of cumene hydroperoxide to form phenol and acetone.

For the purposes of the present invention, reaction mixtures can be either flowable solid, liquid or gaseous materials or combinations of liquid, flowable solid and/or gaseous materials. The reaction mixture can include, for example, starting materials, products, catalysts, solvents and/or inert gases.

Loop reactor systems can, for the purposes of the present invention, include systems which have at least one reactor whose contents are preferably at least partly circulated.

In loop reactor systems, part of the reaction mixture, which may include predominantly starting materials or predominantly products, preferably predominantly products, of at least one reaction that is to take place in the loop reactor system, is preferably circulated via at least one reactor. Predominantly is preferably understood to mean at least 50%, more preferably at least 60%, and most preferably at least 70% of starting materials or products, based on the weight or volume of the reaction mixture.

To circulate the reaction mixture, it is preferable to use equipment such as pumps or blowers. At the outlet from the loop reactor system, it is preferable to connect a container to the circuit in such a way that the reaction mixture which leaves the reactor and/or the reactors can be collected in this container and processed further from this container. Part of the reaction mixture is preferably discharged from the circuit, more preferably downstream of the reactor, into this container. A mass or volume of starting materials and/or catalysts, corresponding to the amount discharged, is preferably fed into the circuit, more preferably upstream of the reactor. This addition can be carried out, for example, by means of at least one metering pump on an equivalent regulation device known to the skilled artisan.

A preferred embodiment is the acid-catalyzed cleavage reaction of cumene hydroperoxide (CHP) to form phenol and acetone, and is described below.

The acid-catalyzed cleavage of CHP is an exothermic reaction, which has a preferable reaction temperature of 40 to 90° C., more preferably 50 to 80° C., most preferably 60 to 70° C. The cleavage reaction is preferably carried out in a loop reactor system which has at least one reactor. It is possible to use all customary types of reactor, and those which are able to remove the heat of reaction liberated in exothermic reactions are preferred. Particular preference is given to reactors which are configured as heat exchangers, i.e. they have a large surface area at which the solution in the reactor can transfer the heat of reaction to a coolant. Coolants which can be used are, for example, water, heat transfer oils or air. Preference is given to using water as coolant.

If the reactors do not remove the heat of reaction, e.g. are not configured as heat exchangers, it may be advantageous to provide at least one heat exchanger in the circuit of the loop reactor system.

In the case of the cleavage of CHP, to start up the loop reactor system by the method of the invention, a reaction mixture that predominantly contains the products, predominantly phenol and acetone, as well as cumene and the catalyst is circulated. With the coolant feed turned off or throttled back in at least one reactor configured as a heat exchanger, a constant or variable amount of at least one starting material and/or at least one catalyst which participates in an exothermic reaction is fed one or more times, continuously or discontinuously, preferably discontinuously, into the circuit upstream of the reactor. At the same time a corresponding mass or corresponding volume of the product mixture which has reacted at this point in time is preferably discharged from the circuit downstream of the reactor and passed to further processing or work-up.

The starting materials and/or catalysts thus added react in the circuit with the evolution of heat. The heat thus liberated in the exothermic reaction heats the reaction mixture circulating in the loop reactor system by a temperature interval corresponding to the amount of heat liberated in the reaction. Preferably, the heat of reaction corresponds to the amount of heat liberated in the exothermic reaction.

The mass or volume of starting materials and/or catalysts to be added, in the case of the cleavage of CHP at least CHP and a catalyst such as sulfuric acid, is determined by the amount of heat introduced into the reaction mixture by the exothermic reaction. The amount of starting materials and/or catalysts to be added is dependent on the total (mass or volume) amount of reaction mixture pumped around the circuit. If the amount of reaction mixture circulated is low, the amount of starting materials and/or catalysts which has to be added to the reaction mixture in order to achieve heating of the reaction mixture by a certain temperature interval is less than in the case of larger amounts of reaction mixture pumped around the circuit.

Preferably, equal mass or volume amounts of the starting material(s) are added over time to the circulating reaction mixture. Put another way, whether measured by mass or volume, it is preferable to always add the same discreet amount of starting material(s) to the circulating reaction mixture. Similarly, and also preferably, equal mass or volume amounts of the catalyst are added over time to the circulating reaction mixture. More preferably, these equal amounts are added over varying time intervals. To control the temperature increase in the reaction mixture being pumped around the circuit, it is most preferable to vary the time interval over which the equal amounts of starting material(s) and/or catalyst(s) are added.

It is likewise preferable to add a different mass or a different volume of starting material(s) and/or catalysts to the reaction mixture being circulated. Put another way, whether measured by mass or volume, it is preferable to add varying amounts of starting material(s) and/or catalyst to the circulating reaction mixture. Particularly preferably, the variable amounts of starting material(s) and/or catalyst(s) are added over fixed time intervals. More particularly preferably, the amounts (equal or variable) are added to the circulating reaction mixture upstream of the reactor such that the at least the starting material(s) are no longer detectable in the reaction mixture leaving the reactor.

During the start-up of the reactor, the temperature is measured continuously or discontinuously, preferably continuously, at various points in the circuit.

After each addition of at least one starting material and/or at least one catalyst to the reaction mixture being circulated, the temperature change in the reaction mixture is measured. The amount of at least one starting material and/or at least one catalyst to be added in the next addition is preferably dependent on the temperature increase resulting from the previous addition.

The addition of starting material mixture to the reaction mixture being circulated is preferably repeated until the circulating reaction mixture has the desired temperature. It is preferred to increase the coolant feed to the reactor on reaching a certain temperature.

The loop reactor system preferably has at least one temperature-measuring apparatus. Preferably, the loop reactor system has at least one temperature-measuring apparatus at least at the inlet or outlet of every reactor and/or heat exchanger present in the loop reactor system.

To start-up of a loop reactor system to be automated, it is preferred to design the temperature-measuring equipment in the loop reactor system so that the results of the measurements may be transmitted to a central control unit, e.g. a process control system. The measurement and the transmission of the data to the control unit can occur discontinuously or continuously, preferably continuously. The central control unit is preferably designed so that the temperature measurements that are received can be compared to the amounts of starting materials and/or catalyst added. In the case of loop reactor systems in which the same reaction is always carried out, it is preferable to install, downstream of the last reactor in the circuit, a measuring apparatus which continuously or discontinuously, preferably continuously, measures the concentration of starting materials and/or catalysts in the reaction mixture at this point in the system and transmits the data to the central control unit. The concentrations can be determined, for example, using an on-line infrared spectrometer.

Preferably, the central control unit includes a computer, a microprocessor, or the equivalent, which, given the teachings herein, may contain program(s) and/or algorithms that automatically control the loop reactor system.

It is preferred to use a central control unit which is able to process the temperature, the amount of starting materials and/or catalysts metered in and the concentration of starting materials and/or catalysts at the outlet of the last reactor From the processed values relating to temperature, starting materials and/or catalysts added and/or the concentration of starting materials and/or catalysts in the reaction mixture after leaving the last reactor the progress of the startup of the loop reactor system can be established and the amount of starting materials and/or catalysts to be metered in and/or the point of metered addition can be determined. The central control unit is preferably designed so that it can control the point in time at which the metered addition and/or the amount of catalysts and/or starting materials to be metered in occurs. Depending on the measured temperature, is preferred for the central control unit to be able to control the coolant flow to the reactors so that when a prescribed temperature is exceeded in the loop reactor system, the temperature can be restored very quickly to the preset temperature by increasing the flow of coolant through the reactor.

It is preferable to design the control unit so that after a prescribed temperature is reached in the loop reactor system, it automatically recognizes the point at which the required degree of heating has been achieved by comparison of the temperature of the reaction mixture and then ends the start-up of the loop reactor system and automatically switches over to steady state operation.

It is preferred to use loop reactor systems in which more than one reactor is present. When at least two reactors are present, they are preferably be connected in parallel or in series. It is preferred to connect a plurality of groups of parallel reactors in series or to connect a plurality of series of reactors in parallel.

Other preferred embodiments, A–M, are described below.

A. Preferably, the reaction components include at least one starting material or at least one catalyst or else at least one starting material and at least one catalyst which are added to the reaction mixture and react exothermically and heat the reaction mixture by means of the heat liberated in the reaction.

B. Preferably, at least one starting material or at least one catalyst or at least one starting material and at least one catalyst which participate in an exothermic reaction is/are added discontinuously to the reaction mixture.

C. Preferably, the addition of at least one starting material or at least one catalyst or at least one starting material and at least one catalyst which participate in an exothermic reaction is carried out at equal time intervals.

D. Preferably, a variable amount of at least one starting material or at least one catalyst or at least one starting material and at least one catalyst which participate in an exothermic reaction is added to the reaction mixture at equal time intervals.

E. Preferably, the addition of at least one starting material or at least one catalyst or at least one starting material and at least one catalyst which participate in an exothermic reaction is carried out at different time intervals.

F. Preferably, a constant amount of at least one selected from the group consisting of starting material and catalyst which participate in an exothermic reaction is added to the reaction mixture at variable time intervals.

G. Preferably, the heat of reaction evolved in the exothermic reaction and introduced into the reaction mixture as a result of the addition of at least one catalyst and at least one starting material of at least one exothermic reaction to a reaction mixture present in a loop reactor system is determined by measuring the temperature at various points in the loop reactor system.

H. Preferably, the measured temperature increase in the reaction mixture is utilized as a measure for the amount of at least one starting material and at least one catalyst to be added.

I. Preferably, the concentration of starting materials in the reaction mixture present in the loop reactor system and the amount of starting materials added to the reaction mixture are monitored.

J. Preferably, the amount of at least one catalyst and at least one starting material or of at least one catalyst or at least one starting material for at least one exothermic reaction added to the reaction mixture is such that the added starting materials and/or the added catalysts are no longer detectable in the reaction mixture at the outlet of at least one reactor in the loop reactor system.

K. Preferably, the measured temperatures, the concentration of starting materials in the reaction mixture and the amount of starting materials added to the reaction mixture are transmitted to a central control unit, the transmitted values are processed in the central control unit and the central control unit controls the amount and/or the point in time of the addition of starting materials to the reaction mixture.

L. Preferably, the central control unit regulates the coolant flow to a heat exchanger present in the loop reactor system.

M. Preferably, the central control unit automatically recognizes the end of the start-up of the loop reactor system by comparison of the temperature of the reaction mixture with prescribed temperature values, ends the start-up of the loop reactor system and automatically switches control over to steady state operation.

EXAMPLES

Having generally described this invention, a further understanding can be obtained by reference to certain specific examples which are provided herein for purposes of illustration only and are not intended to be limiting unless otherwise specified.

Example 1

The method of the invention was used for starting up a loop reactor system in which CHP is to be cleaved into phenol and acetone in the presence of an acid catalyst.

The loop reactor system used contained six reactors connected in series, with the reactors being configured as heat exchangers which are cooled by means of water. The last of the reactors is connected to the first reactor via a circulation line provided with a pump. Upstream of the inlet to the first reactor, the circulation line has two feed points at which the catalyst and the starting material can be introduced into the circulation line or the first reactor by means of metering pumps or equivalent regulation devices. Downstream of the last reactor, an open overflow into a product receiver is provided.

The loop reactor system is charged with 3 m$^3$ of reaction mixture that contains, inter alia, cumene, about 0.1% by weight of catalyst, less than 1% by weight of water, 20% by weight of acetone and 35% by weight of phenol. This reaction mixture was pumped continuously around the circuit at a flow rate of 180 m$^3$/h by means of a pump located in the circulation line. The supply of coolant to the heat exchangers was turned off at the commencement of the start-up of the loop reactor system.

By means of the metering apparatus, 15 kg/h of a 96% strength sulfuric acid and 7 metric tons/h of CHP were introduced continuously for 5 seconds into the circuit of the loop reactor system via the two feed points.

The temperature increase in the reaction mixture achieved by a single addition of CHP was about 3° C.

The metered addition for 5 second periods was repeated until the reaction temperature had been reached in the entire circuit.

Obviously, numerous modifications and variations of the present invention are possible in light of the above teachings. It is therefore to be understood that within the scope of the appended claims, the invention may be practiced otherwise than as specifically described herein.

This application is based on German application 199 11 024.7, filed Mar. 12, 1999, the entire contents of which are hereby incorporated by reference.

What is claimed is:

1. A method of starting up a loop reactor system, comprising:

heating a reaction mixture present in said loop reactor system with the heat of reaction of at least one exothermic reaction occurring in said loop reactor system, wherein, prior to said heating, said reaction mixture comprises at least one product of said exothermic reaction, wherein said product is at least one selected from the group consisting of acetone, phenol, and a mixture thereof, and wherein said heat of reaction is the only heat used during said starting up.

2. The method as claimed in claim 1, further comprising introducing into said reaction mixture at least one selected from the group consisting of a starting material, a catalyst, and a mixture thereof.

3. The method as claimed in claim 2, wherein at least one of said starting material and/or said catalyst participates in said exothermic reaction.

4. The method as claimed in claim 2, wherein said exothermic reaction is initiated by said introducing.

5. The method as claimed in claim 2, wherein said starting material is cumene hydroperoxide.

6. The method as claimed in claim 2, wherein said catalyst is sulfuric acid.

7. The method as claimed in claim 1, wherein, prior to said heating, said reaction mixture comprises at least one selected from the group consisting of a product of said exothermic reaction, a starting material, a catalyst, and a mixture thereof.

8. The method as claimed in claim 7, wherein at least one of said starting material and/or said catalyst participates in said exothermic reaction.

9. The method as claimed in claim 7, further comprising measuring the concentration of at least one of said product, said starting material, and/or said catalyst present in said reaction mixture.

10. The method as claimed in claim 1, therein said exothermic reaction is initiated by introducing to said reaction mixture at least one selected from the group consisting of a starting material, a catalyst, and a mixture thereof, and wherein, prior to said initiation, said reaction mixture comprises predominantly at least one reaction product of said exothermic reaction.

11. The method as claimed in claim 1, further comprising circulating said reaction mixture in said loop reactor system prior to said heating.

12. The method as claimed in claim 1, further comprising determining said heat of reaction by measuring the temperature of said reaction mixture at at least one point in said loop reactor system.

13. The method as claimed in claim 1, further comprising controlling said loop reactor system with a central control unit.

14. The method as claimed in claim 13, wherein said central control unit regulates a coolant flow to a heat exchanger present in the loop reactor system.

15. The method as claimed in claim 13, wherein said central control unit automatically recognizes the end of the start-up of the loop reactor system by comparing a temperature of said reaction mixture with a predetermined temperature, ends the start-up of the loop reactor system and automatically switches control over to a steady state operation.

16. The method as claimed in claim 2, wherein said introducing is at least one selected from the group consisting of adding continuously, adding discontinuously, adding at equal time intervals, adding at unequal time intervals, and a combination thereof.

17. The method as claimed in claim 2, wherein at least one of said starting material, said catalyst, and/or said mixture thereof is introduced in at least one selected from the group consisting of a constant amount, a variable amount, and a combination thereof.

18. The method as claimed in claim 2, further comprising determining an amount of said starting material and/or said catalyst to be introduced by measuring a temperature of said reaction mixture at at least one point in said loop reactor system.

19. The method as claimed in claim 2, further comprising monitoring an amount of at least one of said starting material and/or said catalyst that is introduced.

20. The method as claimed in claim 2, wherein said loop reactor system further comprises an outlet, and wherein at least one of said catalyst and/or said starting material that is introduced is not detectable in said reaction mixture at said outlet.

21. A method of starting up a loop reactor system, comprising:

heating a reaction mixture present in said loop reactor system with the heat of reaction of at least one exothermic reaction occurring in said loop reactor system by introducing into said reaction mixture at least one selected from the group consisting of a starting material, a catalyst, and a mixture thereof, wherein said starting material is cumene hydroperoxide, and wherein said heat of reaction is the only heat used during said starting up.

22. A method of starting up a loop reactor system, comprising:

heating a reaction mixture present in said loop reactor system with the heat of reaction of at least one exothermic reaction occurring in said loop reactor system by introducing into said reaction mixture at least one selected from the group consisting of a starting material, a catalyst, and a mixture thereof, wherein said catalyst is sulfuric acid, and wherein said heat of reaction is the only heat used during said starting up.

23. A method of starting up a loop reactor system, comprising:

heating a reaction mixture present in said loop reactor system with the heat of reaction of at least one exothermic reaction occurring in said loop reactor system, and controlling said loop reactor system with a central control unit, wherein said heat of reaction is the only heat used during said starting up.

24. A method of starting up a loop reactor system, comprising:

heating a reaction mixture present in said loop reactor system with the heat of reaction of at least one exothermic reaction occurring in said loop reactor system, and controlling said loop reactor system with a central control unit, wherein said central control unit regulates a coolant flow to a heat exchanger present in-the loop reactor system, and wherein said heat of reaction is the only heat used during said starting up.

25. A method of starting up a loop reactor system, comprising:

heating a reaction mixture present in said loop reactor system with the heat of reaction of at least one exothermic reaction occurring in said loop reactor system by introducing into said reaction mixture at least one selected from the group consisting of a starting material, a catalyst, and a mixture thereof, wherein said introducing is at least one selected from the group consisting of adding continuously, adding discontinuously, adding at equal time intervals, adding at unequal time intervals, and a combination thereof, wherein said heat of reaction is the only heat used during said starting up.

26. A method of starting up a loop reactor system, comprising:

heating a reaction mixture present in said loop reactor system with the heat of reaction of at least one exothermic reaction occurring in said loop reactor system by introducing into said reaction mixture at least one selected from the group consisting of a starting material, a catalyst, and a mixture thereof, wherein at least one of said starting material, said catalyst, and/or said mixture thereof is introduced in at least one selected from the group consisting of a constant amount, a variable amount, and a combination thereof, and wherein said heat of reaction is the only heat used during said starting up.

27. A method of starting up a loop reactor system, comprising:

heating a reaction mixture present in said loop reactor system with the heat of reaction of at least one exothermic reaction occurring in said loop reactor system by introducing into said reaction mixture at least one selected from the group consisting of a starting material, a catalyst, and a mixture thereof, and monitoring an amount of at least one of said starting material and/or said catalyst that is introduced, wherein said heat of reaction is the only heat used during said starting up.

* * * * *

UNITED STATES PATENT AND TRADEMARK OFFICE
CERTIFICATE OF CORRECTION

PATENT NO. : 6,303,825 B1
DATED : October 16, 2001
INVENTOR(S) : Otto Gerlich et al.

It is certified that error appears in the above-identified patent and that said Letters Patent is hereby corrected as shown below:

Column 1,
Line 17, "acid catalyzed" should read -- acid-catalyzed --.
Line 42, "e.g., in" should read -- e.g. in --.
Line 52, "start up temperature" should read -- start-up temperature --.

Column 5,
Line 2, "that the at least" should read -- that at least --.
Line 24, "To start-up of a loop reactor system" should read -- For the start-up of a loop reactor system --.
Line 50, "reactor" should read -- reactor. --.
Line 54, "reactor the progress of the startup" should read -- reactor, the progress of the start-up --.
Line 61, "temperature, is" should read -- temperature, it is --.

Column 6,
Line 10, "preferably be" should read -- preferably to be --.

Column 8,
Line 36, "therein" should read -- wherein --.

Column 10,
Line 7, "in-the" should read -- in the --.

Signed and Sealed this

Fourth Day of June, 2002

Attest:

JAMES E. ROGAN
Attesting Officer  Director of the United States Patent and Trademark Office